United States Patent
Jiang

(10) Patent No.: US 9,014,335 B2
(45) Date of Patent: Apr. 21, 2015

(54) DUAL MODE SMALL ANGLE SCATTERING CAMERA

(71) Applicant: Rigaku Innovative Technologies, Inc., Auburn Hills, MI (US)

(72) Inventor: Licai Jiang, Rochester Hills, MI (US)

(73) Assignee: Rigaku Innovative Technologies, Inc., Auburn Hills, MI (US)

(*) Notice: Subject to any disclaimer, the term of this patent is extended or adjusted under 35 U.S.C. 154(b) by 139 days.

(21) Appl. No.: 13/912,338

(22) Filed: Jun. 7, 2013

(65) Prior Publication Data

US 2013/0329858 A1 Dec. 12, 2013

Related U.S. Application Data

(60) Provisional application No. 61/657,449, filed on Jun. 8, 2012.

(51) Int. Cl.
*G01N 23/201* (2006.01)

(52) U.S. Cl.
CPC ................... *G01N 23/201* (2013.01)

(58) Field of Classification Search
CPC . G01V 5/0025; G01V 5/0016; G01N 23/203; G01N 23/04; G01N 23/201; A61B 6/483
USPC .......................................... 378/83–90, 73, 78
See application file for complete search history.

(56) References Cited

U.S. PATENT DOCUMENTS

| | | | |
|---|---|---|---|
| 6,014,423 A | 1/2000 | Gutman et al. | |
| 6,041,099 A | 3/2000 | Gutman et al. | |
| 6,330,301 B1 * | 12/2001 | Jiang | 378/85 |
| 6,483,891 B1 * | 11/2002 | Lazarev et al. | 378/37 |
| 6,807,251 B2 | 10/2004 | Okanda et al. | |
| 7,139,366 B1 | 11/2006 | Jiang | |
| 8,094,780 B2 | 1/2012 | Jiang | |
| 8,767,918 B2 * | 7/2014 | Omote et al. | 378/86 |
| 2008/0013685 A1 * | 1/2008 | Iwasaki et al. | 378/86 |
| 2011/0268251 A1 | 11/2011 | He | |
| 2012/0140897 A1 | 6/2012 | Bruegemann et al. | |

OTHER PUBLICATIONS

53rd Annual Denver X-ray Conference, SAXSess—An Analytical Tool for Nanostructured Materials, Aug. 2-6, 2004, Sheraton Steamboat Resort, Steamboat Springs, Colorado.
Anton Paar Brochure, SAXSpace—The modular solution for nanostructure analysis, Nov. 2012, 14 pgs.
Anton Paar Brochure, SAXSess mc² —The Modular Tool for Nanostructure Analysis, 2003, 16 pgs.
PCT International Search Report for International Application No. PCT/US2013/044656, dated Sep. 9, 2013.

* cited by examiner

*Primary Examiner* — Irakli Kiknadze
(74) *Attorney, Agent, or Firm* — Brinks Gilson & Lione

(57) ABSTRACT

A system for analyzing a sample is provided. The system includes a beam selection device for selecting between a one-dimensional operation mode for providing a one-dimensional x-ray beam to the sample and a two-dimensional operation mode for providing a two-dimensional x-ray beam to the sample.

20 Claims, 7 Drawing Sheets

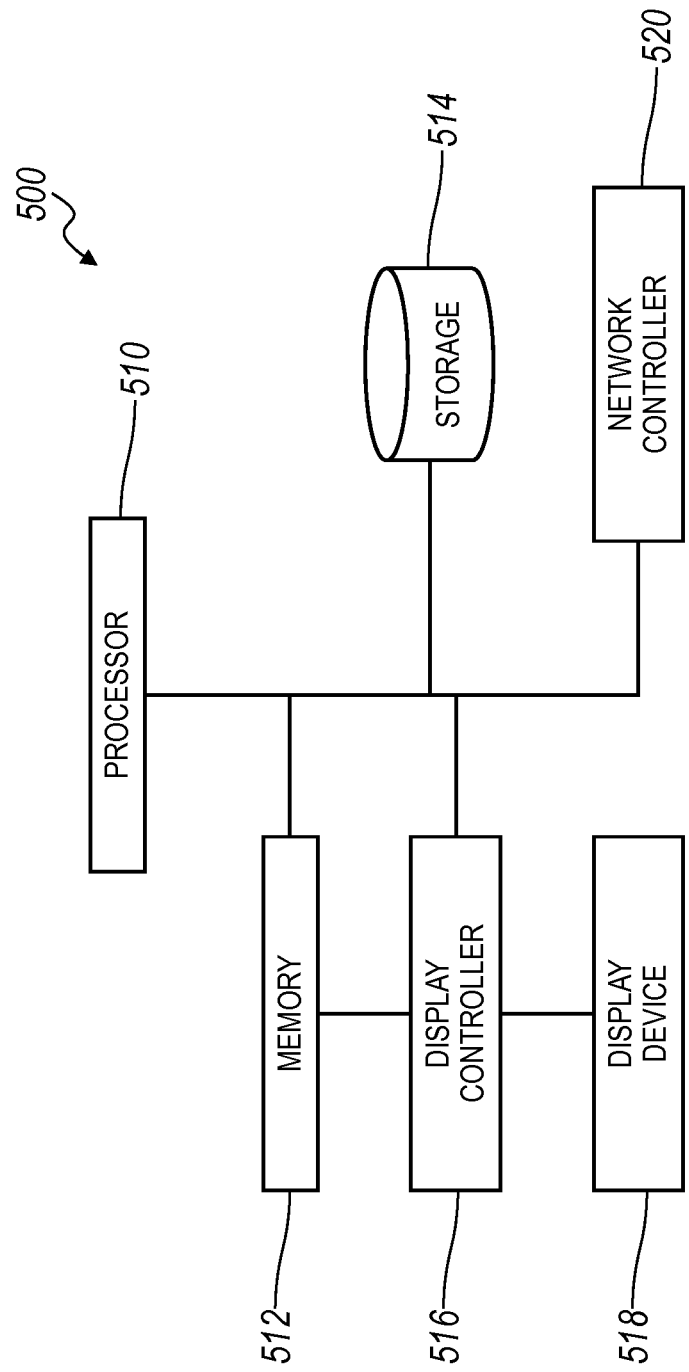

DUAL MODE SMALL ANGLE SCATTERING CAMERA

CROSS REFERENCE TO RELATED APPLICATIONS

This application claims the benefit of U.S. Provisional Patent Application No. 61/657,449 filed Jun. 8, 2012, the content of which is hereby incorporated by reference in its entirety.

BACKGROUND

Field of the Invention

The present application generally relates to a Small Angle X-ray Scattering (SAXS) camera with both one-dimensional capability and two-dimensional capability.

BRIEF SUMMARY

A system for analyzing a sample in the region of small angle x-ray scattering is provided. The system includes a beam subsystem capable of providing a 1-dimensional beam (1D beam) and a 2-dimensional beam (2D beam), and a beam selection device for selecting between the 1D beam for the 1-dimensional operation mode (1D operation mode) and the 2D beam for the 2-dimensional operation mode (2D operation mode).

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 5 is a schematic view of a processing system for implementing the methods described herein.

DETAILED DESCRIPTION

Figure 1:
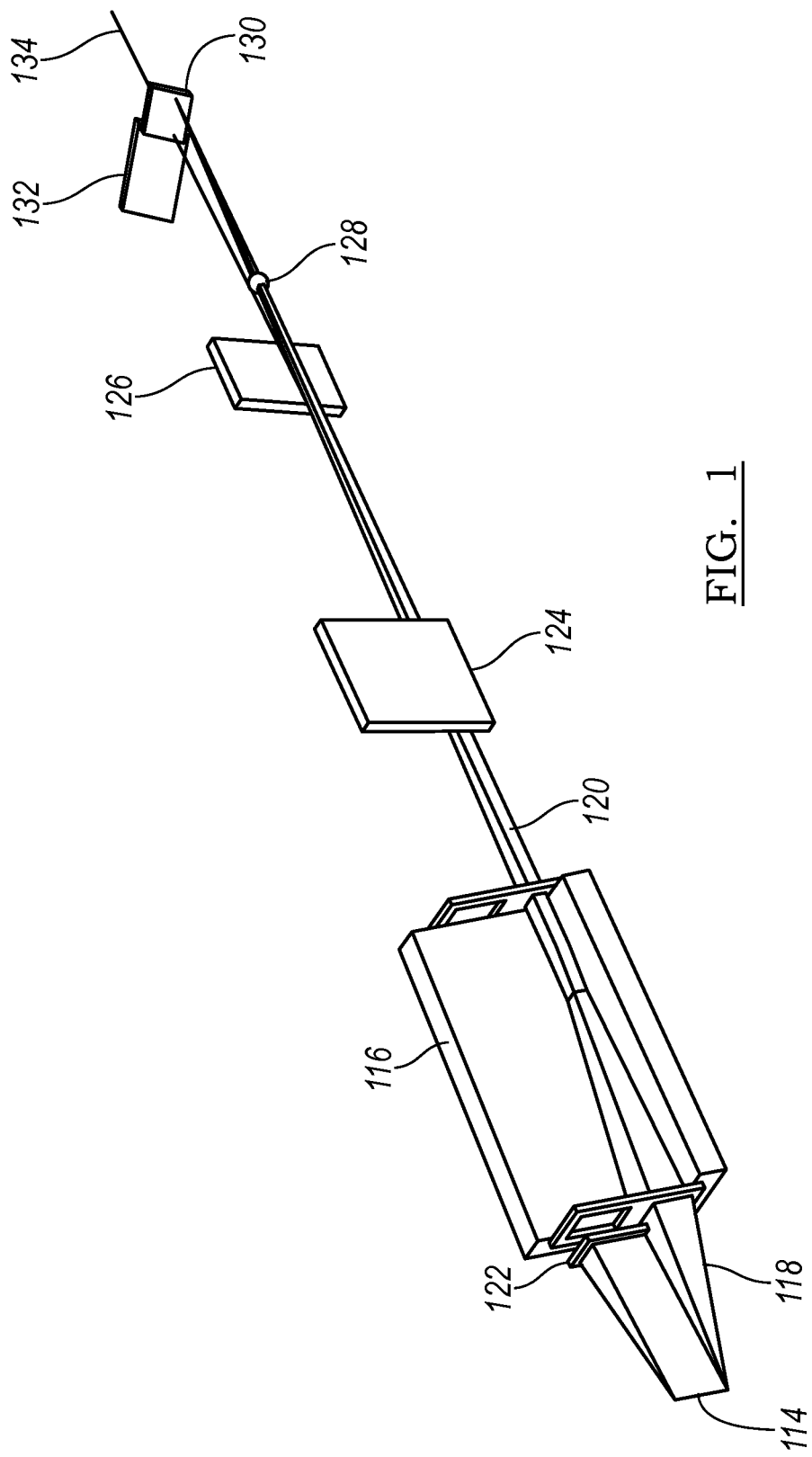
FIG. 1 is a schematic illustration for a small angle x-ray scattering (SAXS) system in the two-dimensional mode.

For a SAXS camera, the performance is typically characterized by the flux, the resolution (defined as the beam diameter at the detector position divided by the sample-to-detector distance), and the system resolution defined by a parameter $Q_{min}$ (defined as $$Q_{min} = \frac{4\pi}{\lambda} \sin\theta_{min},$$

where $\lambda$ is the wavelength and $2\theta_{min}$ is the minimum access angle e.g., the smallest angle, relative to the primary beam, at which meaningful scattering can be collected). In general, increasing the resolution of the system decreases the flux, whereas increasing the flux decreases the system resolution.

To address these issues, a camera known as a Kratky camera using a set of two blocks and an x-ray source having a line projection was developed. The Kratky camera has achieved high resolution, good flux and $Q_{min}$, but it is a one-dimensional camera and, therefore, suffers from smearing. The scattering curve may be obtained from a de-convolution process called de-smearing. Although many de-smearing procedures have been developed, the effectiveness at a low Q region is unavoidably poor. Moreover, because of its one-dimensional nature, a traditional one-dimensional Kratky camera can be used only for isotropic samples.

On the other hand, a pinhole camera, such as three-pinhole systems, can collect data of two-dimensional information. The scattering intensity is a function of the angle between the scattering and the primary beam axis and the azimuthal angle. The pinhole camera eliminates the lateral smearing caused by a one-dimensional beam, and can be used to investigate anisotropic samples. However, the pinhole camera has low flux, low resolution, and its $Q_{min}$ is typically limited to about 0.005 $Å^{-1}$.

U.S. Pat. No. 8,094,780 describes a two-dimensional SAXS camera which is based on a two-dimensional beam and a Kratky alignment system for eliminating parasitic scattering from its data collection zone. The concept offers the two-dimensional capability free from smearing caused by a 1D beam thus the anisotropic specimen analyzing capability and higher flux than a pinhole camera. However, the flux on sample, with a source of the same brilliance, is still much lower, in some instances more than one order of magnitude lower than the traditional one-dimensional Kratky camera. While the two-dimensional SAXS camera is capable of investigating both anisotropic samples and isotropic samples, the high flux of the one-dimensional SAXS camera offers a speed that is critical to some applications, such as in a production environment. It takes a state-of-art rotating anode generator to boost the flux on sample of a two-dimensional SAXS camera to the same level of a one-dimensional SAXS camera with a very inexpensive sealed tube. Such an approach is often cost preventive. In summary, the fundamental limitations of each type of camera have not been overcome: a two-dimensional three-pinhole SAXS camera eliminates smearing and offers the capability to investigate anisotropic samples, a two-dimensional Kratky camera offers improved flux and resolution over a 3-pinhole camera but is still less intense than a one-dimensional Krakty camera if the latter is applicable, and a one-dimensional SAXS camera offers high throughput but only limited to isotropic samples.

A dual mode SAXS camera may be created that includes a source, an optic, a detector, and a pair of anti-parasitic scattering blocks. The source may emit an x-ray beam that is reflected by the optic to form two beams towards a sample. One of the beams can be a two-dimensional beam for which the divergence is controlled by the optic in two orthogonal directions perpendicular to the propagation direction of the beam. The other beam may be a one-dimensional beam for which the divergence is controlled by the optic in one direction only, and the beam is not controlled and/or still divergent in the other direction. A pair of anti-parasitic scattering blocks is positioned between the optic and the sample to create a parasitic-scattering-free space for data collection. The bottom surface of one block may be substantially parallel and co-planned to the top surface of the other block, and either of the blocks is adjustable relative to the beam or the beam is adjustable relative to the blocks for allowing the beam passing through and creating a specific parasitic-scattering-free space. A beam selection mechanism may be inserted either between the source and the optic, or between the optic and anti-parasitic scattering blocks to select a beam. A detector may detect scattering from the sample. The selected beam determines the mode of the camera, providing either a one-dimensional mode or a two-dimensional mode.

Typical two-dimensional beams include two-dimensional focused beam which forms a tight spot at its focus, and two-dimensional collimated beam with low divergence in the direction perpendicular to the propagating beam. The divergence is typically determined by the source size, the design of the optic and the rocking curve width of the optic.

Typical one-dimensional beams include a fan beam of which the source is a point source and the divergence is controlled in one direction only, and a "line" beam of which the source is a line source and the divergence is controlled by the optic in one direction only. A one-dimensional beam typically has a "line" profile at the sample position and the detector position, with dimension in one direction much longer than in the other direction. The ratio is at least 1:4, and typically 1:8 or more. For a one-dimensional beam, the beam can be either focused or collimated in the direction that the divergence is controlled.

U.S. Pat. No. 6,041,099 describes a side-by-side Kirkpatrick Baez (KB) optic for forming a two-dimensional beam. The beam is reflected by both reflectors in two orthogonal directions substantially perpendicular to the beam propagation direction. The working zone for the two-dimensional optic is a narrow strip on each mirror along the junction line of the two reflectors, typically about a few millimeters wide at most, depending on the x-ray energy, d-spacing range, and the mirror length. Outside the working zone, the beam reflected by one mirror will not be reflected by the other mirror. Typically square apertures are attached to either entrance side or exit side or both to block the direct beam (which is not reflected by any mirror) and the residual singly reflected beam (reflected by one mirror only).

A "dual mode" optic can be designed with two reflectors, with one of the two reflectors designed to form a one-dimensional beam and coupled with the second reflector in a Kirkpatrick Baez configuration to form a two-dimensional beam. Both Kirkpatrick Baez and side-by-side Kirkpatrick Baez configurations can be adopted to form the two-dimensional beam, although the side-by-side Kirkpatrick Baez configuration is preferred because of its ability to capture higher flux and smaller optic size. The optic will include an aperture with two openings attached on the entrance side of the optical assembly, or the exit side of the assembly, or both. A selection device, which can be a blade or a slit, is further incorporated into the optical system for selecting the beam. Aperture(s) attached at the entrance and the exit will make the alignment much easier. A four-blade slit can be used to serve as the beam defining aperture as well as the beam selection device.

When a point source is used with the dual mode optic, the one-dimensional beam is a fan beam. Either one aperture at one side or two apertures on both ends may be used to further define the one-dimensional beam and the two-dimensional beam. A fan beam, which is sometimes used for x-ray imaging such as x-ray CT, has not been used for XRD. Careful analysis shows that a fan beam can also be used for x-ray scattering and x-ray diffraction. Compared to the traditional one-dimensional beam or the line beam, there is no additional information loss. On the other hand, the flux on the sample for a fan beam is likely lower than that of a traditional one-dimensional beam since for the latter, the source is long and can have a much higher power loading. One example is that a microfocusing source of 30 um diameter with a copper target may have a power loading 30 W, while a standard Long Fine Focus (LFF) line source has a source projection 40 um×12 mm and has a power loading 2 kW.

When the dual mode optic is used with a line source, the direction of source along the length can be aligned with the reflector designed for a single reflection. Although the other reflector can be aligned towards any point of the source for delivering the x-ray beam, the reflector may be aligned to a point near to the end of the line source when used in the dual mode operation.

It may be preferred to use diffraction optics such as multilayer optics or other bandpass optics such as crystal optics. When the dual mode optic is coupled with a line source, the reflector perpendicular to the line source, e.g. the reflector contributing to the two-dimensional beam only, will reflect x-rays from different parts of the x-ray source at different wavelengths and form a broad and energy dispersive beam. However, the other reflector, as long as it is aligned along the source direction, will form the Bragg condition for the wavelength that the optic is designed for, and therefore form a clean spectrum and a spatially well-defined two-dimensional beam.

When the dual mode optic is coupled to a point source, the beam selection mechanism, which can be as simple as a plate to block one beam and let the other beam through, can be positioned between the source and the optic, or between the optic and the anti-parasitic scattering blocks. When the dual mode optic is coupled to a line source, the beam selection mechanism is preferably positioned between the source and the optic since otherwise, the x-rays passing through the aperture of the one-dimensional beam at the entrance side could also pass through the aperture of two-dimensional beam at the exit side.

The two-dimensional beam can be steered to different directions by arranging the relative angle between the reflector which contributes to only the two-dimensional beam and the reflector which contributes to both the two-dimensional beam and the one-dimensional beam. The optic can be designed with the one-dimensional beam and the two-dimensional beam crossing each other at a specific location, for instance, at the sample position or at the detector position.

As U.S. Pat. No. 8,094,780 described, the anti-parasitic scattering blocks may include two blocks with well finished planar surfaces. The two surfaces are opposite to each other and substantially aligned, e.g. two surfaces are aligned to be in the same plane. When a beam of x-rays passing through the opening between the two blocks, the scattered x-rays from the corners of the blocks are blocked by the surface of the block near the sample. The angle between the surface of the block near the sample and the primary beam axis determines the minimum angle at which the data can be collected free of parasitic scattering. The anti-parasitic scattering blocks may be typically designed and fabricated as one integrated piece. Typically it is made by attaching a flat block to a "U" shaped block. The well-machined flat surface of the "U" shaped block and the flat surface of the first block ensure that the two opposite surfaces are well aligned. This integrated piece is typically called a Kratky block or sometimes Kratky collimation block. In the dual mode SAXS camera, the one-dimensional beam may be aligned with the two-dimensional beam. The plane in which both the one-dimensional and two-dimensional beams are located can be called a beam plane. The beam plane should be aligned at an angle with the common plane defined by the surface of the first Kratky block and the surface of the second Kratky block (we may call this Kratky plane). Either the Kratky block can be adjusted relative to the beams or the beams can be adjusted relative to the Kratky block. It may be preferred to be able to rotate the Kratky blocks about a pivot axis parallel to the beam plane and perpendicular to the beam axis so that the angle between the beam axis (or beam plane) and the Kratky plane can be easily and continuously adjusted. Changing the angle between the Kratky plane and the beam axis alters the minimum access angle and, therefore, $Q_{min}$; and it also alters the opening of the Kratky blocks to the beam, therefore, the flux on the sample. The adjustment of the Kratky blocks' angular position relative to the beam changes the trade-off between the $Q_{min}$ and flux on the sample. It is preferred to have the pivot axis between the two edges of the Kratky blocks. However, the pivot can be anywhere along the beam propagation direction.

Sample handling can be an important part of the SAXS system. The sample handling system should be able to position the sample both in the paths of the one-dimensional beam and the two-dimensional beam. This may be as simple as mechanical markers for different modes of operations or a translation stage which can position the sample to different positions pertinent to the operation mode. In the two-dimensional mode, if an anisotropic sample is studied, a rotation freedom about the primary beam axis may be used for acquiring the full 360 degrees of data. Other sample handling systems, such as grazing incident stages, or sheer-stress cell and many other standard accessories for SAXS, can be integrated to the system.

It is preferred to use a two-dimensional detector, especially a solid state photon counting pixelated detector. Such a detector has the merits of high resolution, ultra-low noise, real time measurement and fast counting rate. Even with the one-dimensional operation mode, the two dimensional detector offers the merit of easy alignment. The alignment between one-dimensional beam and the detector is not critical since the data is collected in two dimensions, and one can find the orientation of the line beam from the two-dimensional image created from the scattering.

A one-dimensional detector, which is also called linear detector, can also be used for the camera as well. Two problems arise with using a one-dimensional detector. For the one-dimensional mode, it is critical to align the orientation of the line beam with the detector cell. Otherwise the resolution suffers. For the two-dimensional mode, using a one-dimensional detector would not be able to acquire the two-dimensional data. One solution would be using a slit in front of the detector and then to scan the data field to create a two-dimensional image. The scanning can be done linearly or angularly with the rotation center at the center of the primary beam. When scanning angularly, the slit opening in front of the detector can be in the form of constant angle, e.g. polar scan. One merit to using a linear detector is its low cost.

The biggest benefit of the dual mode SAXS camera is its full capacity of offering high flux in the one-dimensional mode and two-dimensional capability in the two-dimensional mode at a cost not much higher than one system. Some embodiments of the system may also have one or more of the following benefits. When a point source is used, the system may have an optimized two-dimensional performance and yet may offer much higher flux in the one-dimensional mode than in the two-dimensional mode. When a line source is used, the system offers the optimized performance of the one-dimensional mode, and yet offers the two-dimensional capability. For many unknown samples, one can quickly try with one of the two operation modes for a quick check and determine which mode is the best for the work. The camera can be used to investigate anisotropic materials and can be configured into a high resolution reflectometer, or a high resolution reflective SAXS camera. Since the overall camera length is much shorter than a pinhole camera, the system has a large angular range or large Q range. The system can be extended from small angle scattering measurement to wide angle scattering measurement.

As such, one embodiment of the envisioned probe beam system includes a source, two one-dimensional reflectors in Kirkpatrick Baez configuration for the portion of the optic delivering a two-dimensional beam, preferably in a side-by-side configuration, and an aperture having two openings, one for the two-dimensional beam which is reflected by both mirrors and one for the one-dimensional beam which is reflected by one mirror only. In addition, a selection mechanism, either a blade, or a slit, is used to select one of the two beams.

Now referring to FIG. 1, a view of the dual mode small angle x-ray scattering system in a two-dimensional operation mode is provided. The small angle x-ray system includes an x-ray source 114, an optic 116, Kratky blocks 124,126, and a detector 132. The x-ray source 114 may be a line source or a point source. The source 114 may emit a divergent beam 118 that is received by an optic 116. The optic 116 may be a two-dimensional optic which conditions the beam in two orthogonal dimensions perpendicular to the beam propagation. In addition, one of the one-dimensional reflectors is designed with the width capable of conditioning the beam in one dimension perpendicular to the direction of the beam propagation. The optic 116 may be a crystal optic or a multilayer optic. Further, the optic 116 may be a KB side-by-side or sequential optic. A beam selection device 122 may be used for selecting one of the two beams (e.g. the line beam or the point beam). The beam selection device 122 may be controlled to select various portions of the beam, or it may select one of the split beams at the beam splitting position. The beam selection device 122 may be a shutter or movable beam stop that is controlled by an actuator to select between the one-dimensional mode and the two-dimensional operation mode. At least a portion of the beam is allowed through the beam selection device 122, interacts with optic 116 and then interacts with the first block 124 of the pair of Kratky blocks 124, 126. In FIG. 1, the beam selection device 122 selects the two-dimensional beam (also sometimes called a point beam). The first surface of the first Kratky block 124 interacts with x-rays to define one side of the x-ray beam. The beam is also defined by the edge of the first surface of the second block 126. The first surface of the second block 126 may be located substantially in plane with the first surface of the first block 124 therefore the first surface of the block 124 and the first surface of the block 126 create a parasitic scattering free zone beyond the plane which may be called the "Kratky plane". Line 134 is a projection of the primary beam on to the Kratky plane. The angle between line 134 and the primary beam is $2\theta_{min}$. It is understood that block 124 may be an edge or other device such that the tip of the edge extends substantially in plane with the first surface of the second block 126. The beam stop 130 may extend to the kratky plane at 134 (the parasitic scattering free plane). The sample 128 may cause scattering of the beam which may be received by detector 132. A portion of the beam will continue through the sample and be received by the beam stop 130. The beam stop is used to block the portion of the beam that is directly transmitted through the sample without being scattered into the parasitic scattering free zone, so the detector 132 will not be over saturated and the detection of the scattering from the sample 128 will not be interfered.

Figure 2:
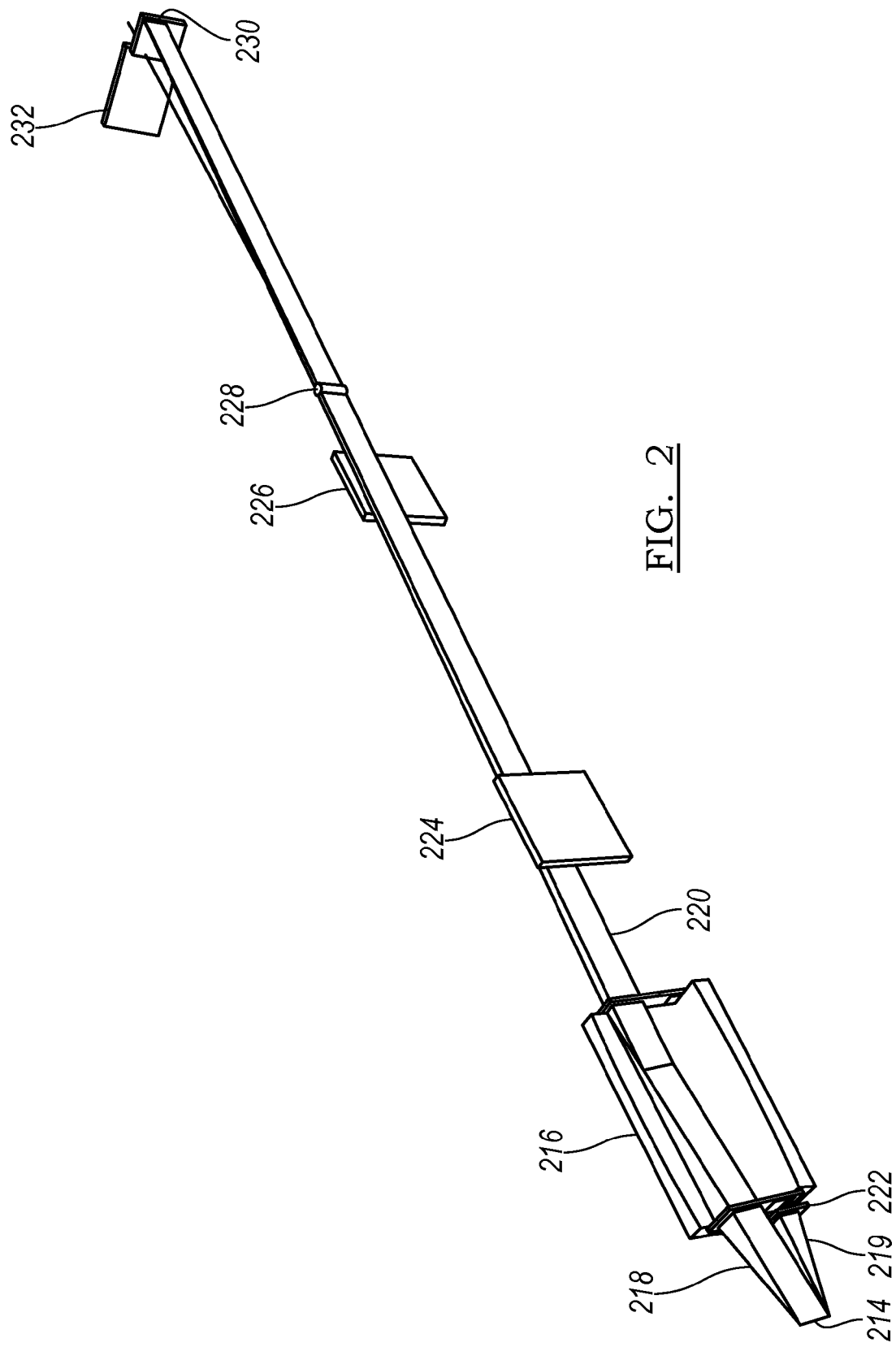
FIG. 2 is a schematic illustration for a small angle x-ray scattering system in the one-dimensional mode.

Now referring to FIG. 2, a view of a dual mode small angle x-ray scattering system in a one-dimensional operation mode is provided. The line source 214 projects an x-ray beam with a first portion 218, and a second portion 219, and a beam selection device 222 may block the second portion 219 (that forms the two-dimensional beam) and allow the first portion 218 (that forms the one-dimensional beam such as a line beam) to project on the optic 216. The optic 216 conditions the first portion 218 to form a one-dimensional beam, and directs it toward the Kratky blocks 224 and 226. The one-dimensional beam 220 may interact with the first Kratky block 224 and the second Kratky block 226 and form a parasitic scattering free zone. Further, a portion of the beam may continue to the sample 228. The one-dimensional beam 220 may interact with the sample 228 to generate scattering that is collected by the detector 232. Further, the direct portion of the one-dimensional beam 220 that passes through the sample may be blocked by the beam stop 230.

Figure 3A:
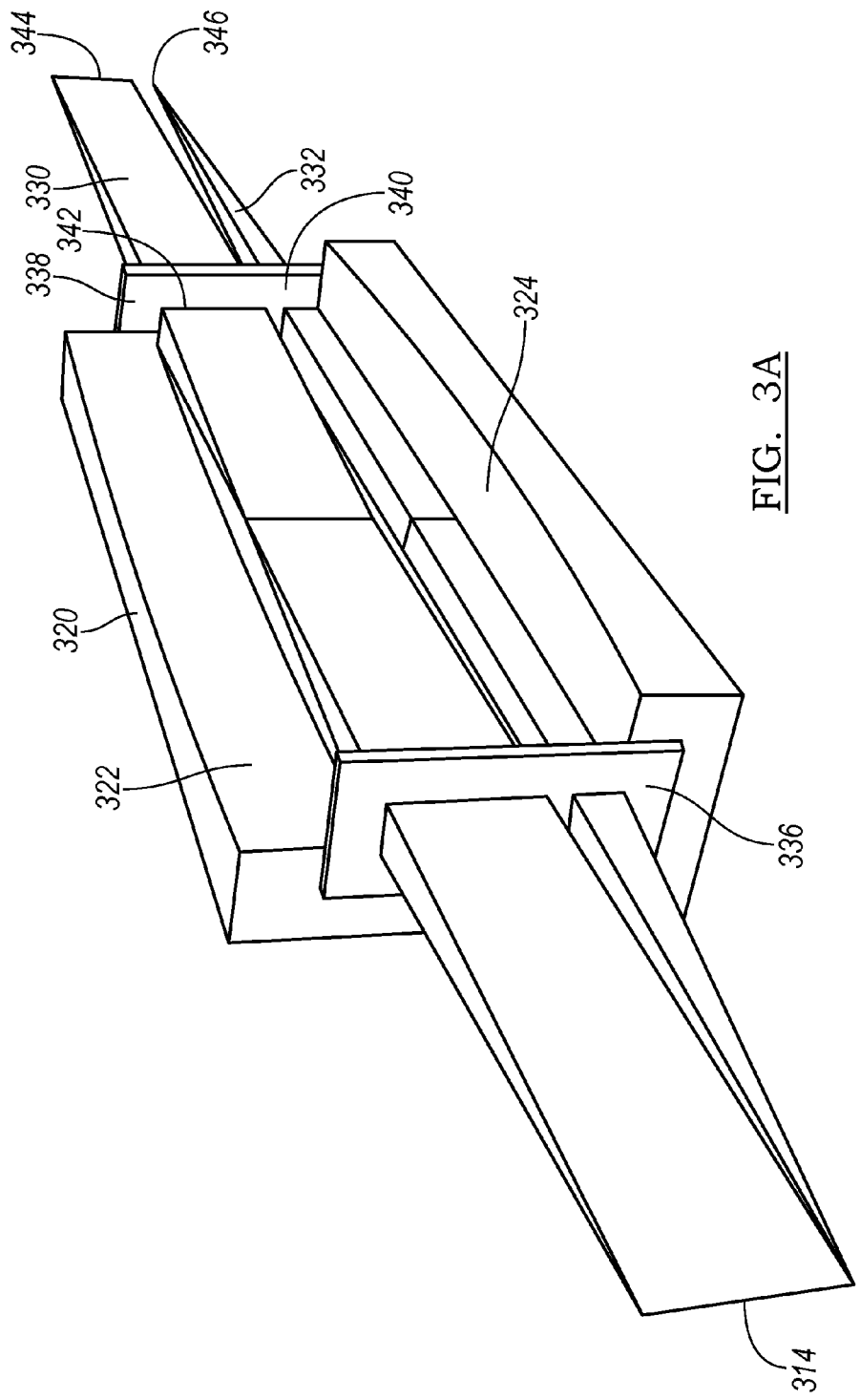
FIGS. 3A and 3B are a schematic illustration of an optical system for a SAXS system using a line source.

Now referring to FIG. 3A, one possible embodiment of the dual mode beam assembly comprises an x-ray source 314 and optic 320. The source 314 is a line source which emits an x-ray beam towards the optic 320. The x-ray beam from the source 314 interacts with an aperture 336 having a first opening and a second opening therein. The first opening may be an elongated opening for the x-rays that would form a one-dimensional beam. The second opening may be a hole such as a square hole for the two-dimensional beam. Accordingly, the x-ray beam from the source 314 may be reflected into a one-dimensional beam 330 and a two-dimensional beam 332. The optic 320 serves as both a two-dimensional optic and a one-dimensional optic, for example, a side-by-side KB configuration with one mirror designed with extended width capable of reflecting x-rays to form a one-dimensional beam. Accordingly, the source 314 and the aperture 336 may be aligned such that the one-dimensional beam 330 is formed by a first surface 322 of the optic while the two-dimensional beam 332 is formed by both the first surface 322 and the second surface 324 of the optic. Accordingly, the one-dimensional beam 330 may be conditioned, for example focused or collimated, by the first surface 322 and is further defined by the aperture 338. Similarly, the two-dimensional beam 332 may be conditioned by both the first surface 322 and the second surface 324 in two orthogonal directions perpendicular to the beam propagation direction and directed to the aperture 338. The exit aperture 338 includes a first opening 342 and a second opening 340. In this instance, the one-dimensional beam 330 is shown as being focused to a line 344 while the two-dimensional beam 332 is shown as being focused to a point 346. Accordingly, one of the one-dimensional beam 330 and the two-dimensional beam 332 may be selectively allowed to pass through the optical system and interact with the Kratky blocks and sample as discussed elsewhere in this application.

In the case of a line source as shown in FIG. 3A, the optic may be aligned to the source in such a way that one of the two mirrors is in-line with the line source (or in parallel to the source), and the other mirror is aligned perpendicular to the line source. This one-dimensional beam, which is reflected by the mirror parallel to the line source only, is a typical one-dimensional beam used by many powder diffractometers and the conventional one-dimensional Kratky camera. The beam can be a collimated beam or a focused beam. The divergence in the axial plane, e.g. the direction perpendicular to the diffraction plane of the mirror or in the direction of the line source, is normally defined by a slit at the optic exit. A Soller slit is also often used for further defining the axial divergence.

The two-dimensional beam may be formed with a line source by aligning the optic to any point of the line source. However, it may be preferred to align the optic to one end of the source.

A line source beam system provides a much higher intensity for the one-dimensional beam than a point source beam system. However, the quality of the two-dimensional beam, due to the relatively lower brilliance compared to a point source and the large dimension of the source in one direction, may not be as good as when using a point source. The beam flux would be lower and the spectral background would be higher.

The fact that one mirror is aligned parallel to the line source and the other mirror is aligned perpendicular to the line source may give the best performance for this configuration. In the diffraction plane of the mirror perpendicular to the line source, Bragg condition can be satisfied with a large portion of the source along the line source at different wavelengths, therefore a broad range of spectrum will be reflected and the beam divergence is high in this direction. However, only the x-rays at the working energy that the optic is designed for can be reflected by the mirror parallel to the line source. Consequently, the spectrum of the output beam is largely determined by the source width of the line source, which is normally designed to be very small, for example 40 micron for a fine focus sealed tube or a long fine focus sealed tube. The mirror parallel to the line source acts as a spectral filter and "spatial filter" to eliminate the majority of the x-rays of outside the narrow energy range for which the optic is designed.

An aperture with two openings, one for the x-rays that form the one-dimensional beam and the other for the x-rays that form the two-dimensional beam, can be attached to the entrance side of the optic. A similar aperture can also be attached to the exit side of the optic. These apertures occlude the direct beam from the source and further define the beam spatially. A beam selection device is used to select one of the two beams. It is preferred to have the beam selection device installed between the source and the optic. Otherwise, the singly reflected beam could pass through the aperture of the two-dimensional beam at the exit end and create unwanted background noise. An exception to this is if there is additional downstream device to block the x-rays from the one-dimensional aperture at the entrance side.

Alternatively, a slit can be designed and applied to the optic to serve both as the beam defining aperture and the beam selection shutter. For example, a two-blade slit with a fixed long slit has the freedom to form an aperture either for the two-dimensional beam or for the one-dimensional beam before or after the optic. The slit can serve both functions: occlude unwanted beam, and let only one of the beams pass through. A 4-blade slit or shutter would be able to serve the same function.

Figure 3B:
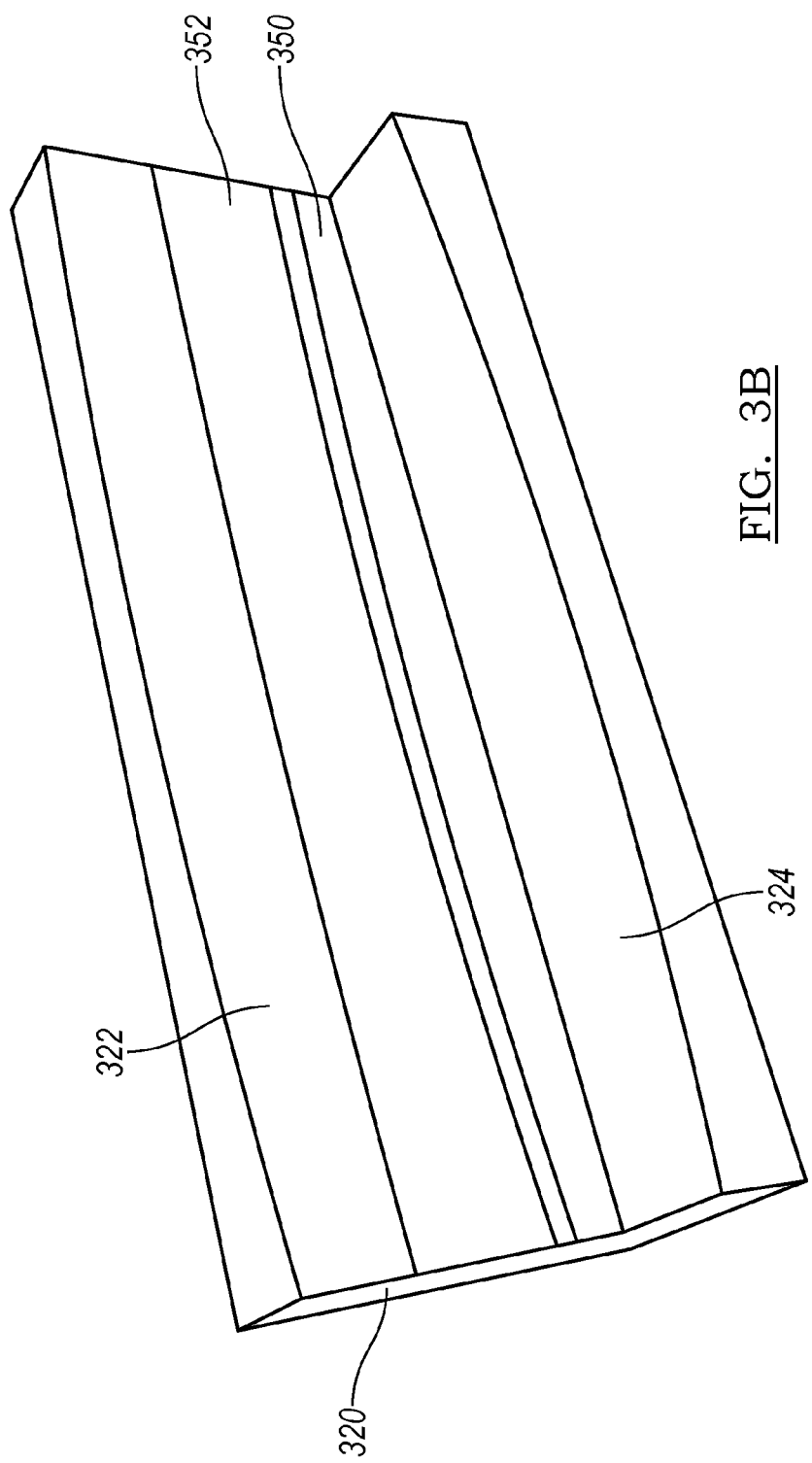

Now referring to FIG. 3B, a view of the optic 320 is provided. The first surface 322 may be perpendicular to the second surface 324. Further, both the one-dimensional beam 330 and the two-dimensional beam 332 may interact with the first surface 322. The one-dimensional beam 330 may interact with a first portion of the surface 352 while the two-dimensional beam 332 may interact with a second portion of the surface 350. The first portion of the surface 352 may be further away from the corner of the optic 320 than the second portion of the surface 350. In addition, the first portion of the surface 352 may have no overlapping with the second portion of the surface 350. However, the first portion of the surface 352 may have, but not necessarily, a continuous contour and/or multi-layer coating as the second portion 350 of the surface 322.

Figure 4A:
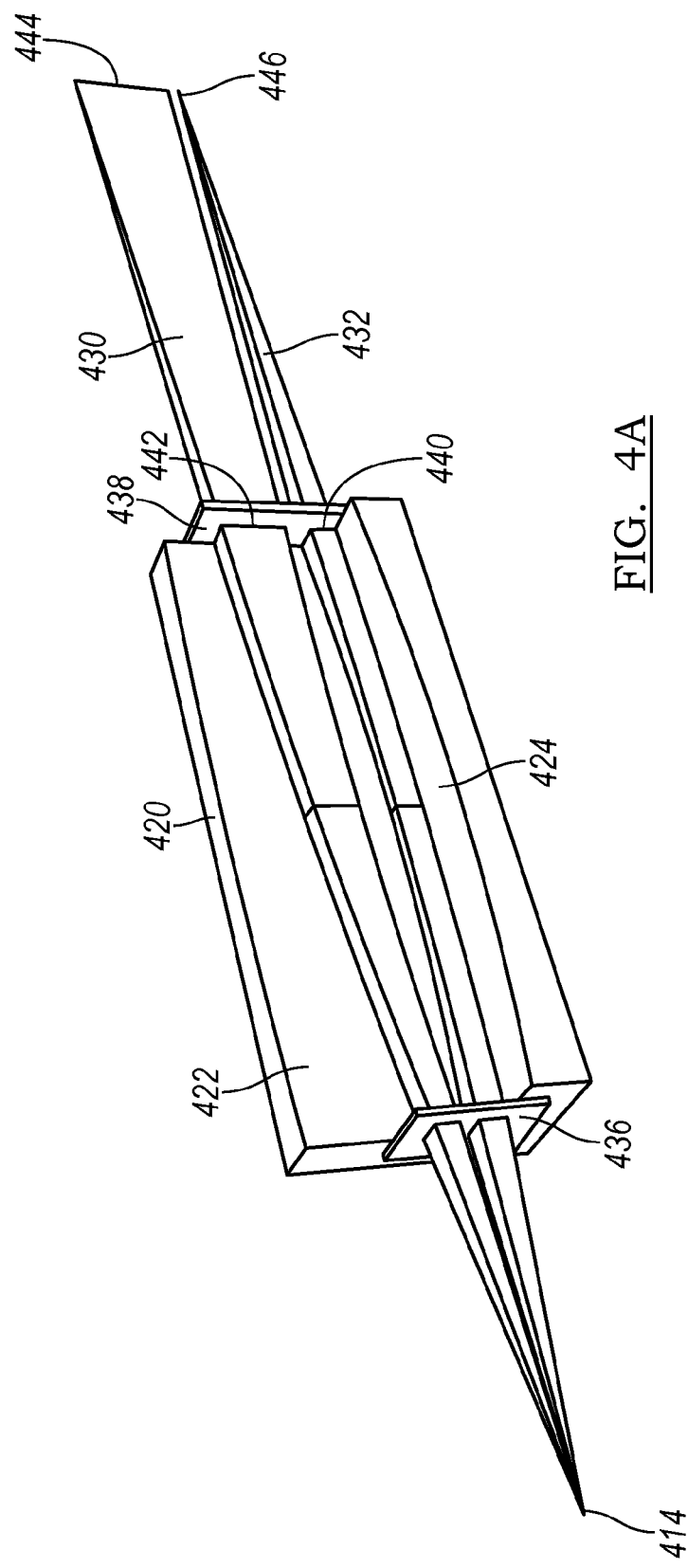
FIGS. 4A and 4B are a schematic illustration of an optical system for a SAXS system using a point source.

Now referring to FIG. 4A, one possible embodiment of the x-ray beam system is provided with respect to an x-ray point source 414 and optic 420. The source 414 is a point source which emits x-rays that expands from a point towards the optic 420. Accordingly, the x-rays from the source 414 may be split into a first portion that forms the one-dimensional beam 430 and second portion that forms a two-dimensional beam 432. The first portion that forms the one-dimensional beam 430 and the second portion that forms the two-dimensional beam 432 may be received by the optic 420. The optic 420 serves both as a one-dimensional optic and a two-dimensional optic. The optic may be in the form of KB configuration for example a side-by-side KB optic, with one mirror of extended width capable of providing both one-dimensional beam and working with the other mirror to provide the two-dimensional beam. Accordingly, the source 414 and the aperture 436 may be aligned such that the one-dimensional beam 430 interacts with the first surface 422 of the KB optic while the two-dimensional beam 432 interacts with both the first surface 422 and the second surface 424 of the KB optic. Accordingly, the one-dimensional beam 430 may be conditioned, for example focused or collimated, by the first surface 422 and directed to the exit aperture 438. Similarly, the two-dimensional beam 432 may be conditioned by both the first surface 422 and the second surface 424 in two perpendicular directions orthogonal to the propagation direction and directed to the exit aperture 438. A beam selection device (such as a blade or a shutter) may be controlled to selectively block one or both of the first portion of x-rays that form the one-dimensional beam 430 and the second portion of x-rays that form two-dimensional beam 432 at the entrance side, or one-dimensional beam 430 and the two-dimensional beam 432 at the exit side. In this instance, the one-dimensional beam 430 is shown as being focused to a line 444 while the two-dimensional beam 432 is shown as being focused to a point 446. Accordingly, one of the one-dimensional beam 430 and the two-dimensional beam 432 may be selectively allowed to pass through the beam selection shutter and interact with the Kratky blocks and sample as previously discussed elsewhere in this application.

In the case of a point source as shown in FIG. 4A, the one-dimensional beam, which is reflected by one mirror only, is a "fan beam". The two-dimensional beam with a point source may be a better defined beam spectrally and spatially compared to the case with a line source. The one-dimensional beam, or the fan beam, has the merit of better spatial definition, e.g. less crossed x-rays caused by the long line source.

The point source based beam solution may offer both one-dimensional beam and two-dimensional beam. The optic may be in the form of a side-by-side Kirkpatrick Baez optic with one mirror capable of providing the one-dimensional beam and working with other mirror to provide the two-dimensional beam. Schematically the upper beam is a one-dimensional beam, reflected by the vertical mirror only. The beam schematically shown interacting with the corner of the optic is a two-dimensional beam, reflected by both mirrors in the orthogonal directions to form a focus. An aperture having two openings further defines the beams. The apertures shown are on the both sides of the optic, but it could be on either the entrance side, or the exit side, or both. A selection mechanism, either a blade or a slit (not shown), could be used to select either the one-dimensional beam or the two-dimensional beam.

A focused beam is shown in the picture. The one-dimensional beam is divergent along the vertical direction ("fan beam") and focused in the horizontal plane. However, the two mirrors can be any combination of elliptical mirrors and parabolic mirrors. The one-dimensional beam could be either a "focused fan beam" or "collimated fan beam". The two-dimensional beam could be either a focused beam, or a collimated beam, or a beam focused in one direction and collimated in the other direction.

It may be preferred to have an aperture with two openings attached on the entrance side of the optical assembly, or the exit side of the assembly, or both, and a selection device, which can be a blade or a slit, may be further incorporated into the optical system for selecting the beam. Aperture(s) attached at the entrance and exit can make the alignment much easier. A four-blade slit can be used to serve as the beam defining aperture as well as the beam selection device.

Figure 4B:
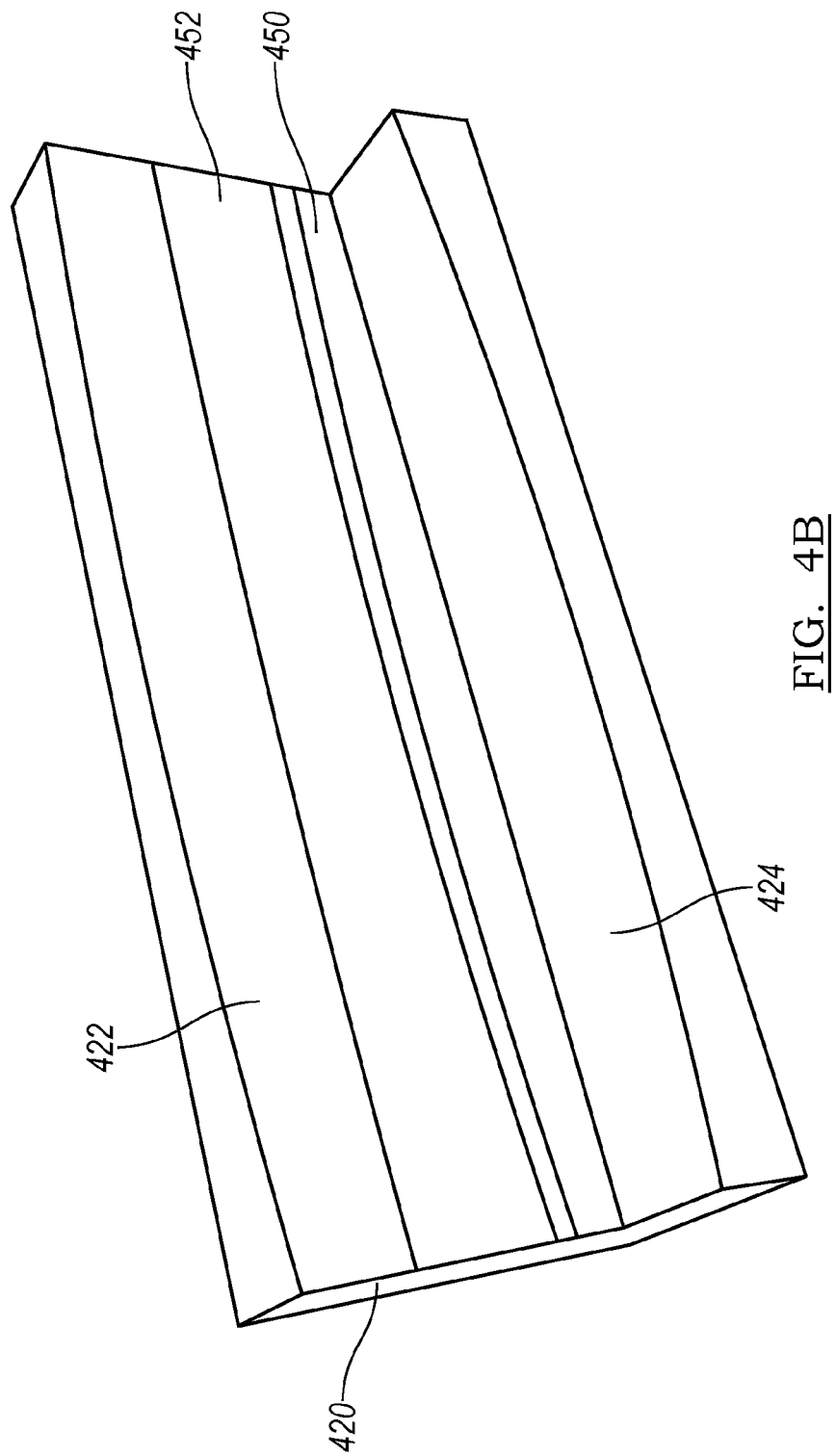

Now referring to FIG. 4B, a view of the optic 420 is provided. The first surface 422 may be perpendicular to the second surface 424. Further, both the one-dimensional beam 430 and the two-dimensional beam 432 may interact with the first surface 422. The one-dimensional beam 430 may interact with a first portion of the surface 452 while the two-dimensional beam 432 may interact with a second portion of the surface 450. The first portion of the surface 452 may be further away from the corner of the optic 420 than the second portion of the surface 450. In addition, the first portion of the surface 452 may have no overlapping with the second portion of the surface 450. However, the first portion of the surface 452 may have, but not necessarily, a continuous contour and/or multi-layer coating as the second portion 450 of the surface 422.

In addition, a controller may be configured to control an actuator to move the beam section device between a one-dimensional operation mode and a two-dimensional operation mode. Further, the controller may be instructed to change between the one-dimensional operation mode and the two-dimensional operation mode based on the measurement characteristics received by the detector, for example based on scattering data such as the scattering pattern or intensity data. The controller may be also configured to communicate with a motion device, such as a motorized stage, to rotate the sample around the primary beam axis when the controller is switched to the two-dimensional mode. In addition, the controller may also control a motion device, such as a motorized stage, to move the sample between the first and second location based on the selection of the one-dimensional and two-dimensional operation mode. The beam stop can also be positioned based on the resolution setting as well as the operation mode.

Any of the controllers, control circuits, modules, servers, or engines described may be implemented in one or more computer systems or integrated controllers. One exemplary system is provided in FIG. 5. The computer system 500 includes a processor 510 for executing instructions such as those described in the methods discussed above. The instructions may be stored in a computer readable medium such as memory 512 or storage devices 514, for example a disk drive, CD, or DVD, or in some form of nonvolatile memory, internal or external to the processor, such as EPROM or flash. The computer may include a display controller 516 responsive to instructions to generate a textual or graphical display on a display device 518, for example a computer monitor. In addition, the processor 510 may communicate with a network controller 520 to communicate data or instructions to other systems, for example other general computer systems. The network controller 520 may communicate over Ethernet or other known protocols to distribute processing or provide remote access to information over a variety of network topologies, including local area networks, wide area networks, the Internet, or other commonly used network topologies.

In other embodiments, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system or processor. Further, in an exemplary, non-limited embodiment, implementations can include distributed processing, component/object distributed processing, and parallel processing. Alternatively, virtual computer system processing can be constructed to implement one or more of the methods or functionality as described herein.

Further, the methods described herein may be embodied in a computer-readable medium. The term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

As a person skilled in the art will readily appreciate, the above description is meant as an illustration of the principles for this application. This description is not intended to limit the scope or application of this disclosure in that the system is susceptible to modifications, variations and changes, without departing from the spirit of this application.

I claim:

1. A dual mode SAXS camera for analyzing a sample, the camera being capable of providing both a one-dimensional operation mode and a two-dimensional operation mode comprising:
    an x-ray source;
    an optical system receiving x-rays from the source, and capable of providing both one-dimensional beam and two-dimensional beam on to the sample;
    a selection device to select either the one-dimensional beam or the two-dimensional beam;
    a detector to collect the scattering data from the sample; and
    a Kratky anti-parasitic scattering system between the optical system and the detector to create a data collection zone free of parasitic scattering, wherein the sample position is located between the Kratky anti-parasitic scattering system and the detector.

2. The camera of claim 1, wherein the optical system comprises two one-dimensional reflectors, one of the reflectors reflects a first portion of the x-rays to form a one-dimensional beam, and coupled with the other reflector in Kirkpatrick Baez configuration and reflects a second portion of the x-rays to form a two-dimensional beam.

3. The camera of claim 2, wherein the Kirkpatrick Baez configuration is the side-by-side configuration.

4. The camera of claim 2, wherein the two one-dimensional reflectors are multilayer optics.

5. The camera of claim 2, wherein at least one of the one-dimensional optics is a crystal optic.

6. The camera of claim 2, wherein the optical system has an aperture with two openings, the first opening being a one-dimensional beam opening and the second opening being a two-dimensional beam opening.

7. The camera of claim 6, wherein the aperture is installed at the entrance side of the optic.

8. The camera of claim 6, wherein the aperture is installed at the exit side of the optic.

9. The camera of claim 2, wherein the optical system is equipped with two apertures, the first aperture is installed at an entrance side of the optical system and a second aperture is installed at an exit side of the optical system.

10. The camera of claim 1, wherein the x-ray source is a point source.

11. The camera of claim 1, wherein the x-ray source is a line source.

12. The camera of claim 1, wherein the beam selection device is located between the source and the optical system.

13. The camera of claim 1, wherein the beam selection device is located between the optic and the Kratky anti-parasitic scattering system.

14. The camera of claim 1, further comprising a beam stop to block the direct beam.

15. The camera of claim 1, further comprising a motion device which rotates the sample around the beam axis of the two-dimensional beam for an anisotropic sample.

16. The camera of claim 1, wherein the detector is a two-dimensional detector.

17. The camera of claim 1, wherein the detector is a one-dimensional detector.

18. The camera of claim 17, wherein the one-dimensional detector is equipped with a narrow slit and a linear or polar motion for scanning.

19. The camera of claim 1, wherein the Kratky anti-parasitic scattering system can rotate about a pivot point.

20. The camera of claim 1, wherein the one-dimensional beam is centered with the two-dimensional beam at a certain distance from the dual mode optic.

* * * * *